United States Patent [19]

Sirota

[11] Patent Number: 4,737,131
[45] Date of Patent: * Apr. 12, 1988

[54] TOY

[76] Inventor: Vladimir Sirota, 130 W. 67 St., New York, N.Y.

[*] Notice: The portion of the term of this patent subsequent to Jul. 22, 2003 has been disclaimed.

[21] Appl. No.: 858,733

[22] Filed: May 2, 1986

Related U.S. Application Data

[63] Continuation-in-part of Ser. No. 734,173, May 15, 1985, Pat. No. 4,601,668.

[51] Int. Cl.$^4$ ..................... A63H 3/28; A63H 33/26
[52] U.S. Cl. ..................... 446/130; 446/485; 446/303; 446/295
[58] Field of Search ............ 446/14, 26, 130, 175, 446/295, 296, 297, 301, 303, 304, 472, 219, 485; 434/262, 266; 340/521, 628, 573, 575; 353/74

[56] References Cited

U.S. PATENT DOCUMENTS

| | | | |
|---|---|---|---|
| 1,900,353 | 3/1933 | Marchetti | 446/175 |
| 2,668,689 | 9/1954 | Christopher | 40/579 X |
| 3,184,886 | 5/1965 | Weih | 446/295 |
| 3,298,132 | 1/1967 | Elwell | 446/295 |
| 3,514,899 | 6/1970 | Bonanno et al. | 446/304 X |
| 3,538,639 | 10/1970 | Tomaro | 446/175 |
| 3,665,087 | 5/1972 | Poylo | 434/262 X |
| 4,155,196 | 5/1979 | Bollinger et al. | 446/295 X |
| 4,264,904 | 4/1981 | McCoy et al. | 340/573 X |
| 4,303,946 | 12/1981 | Berry | 353/74 X |
| 4,601,668 | 7/1986 | Sirota | 446/472 X |
| 4,605,380 | 8/1986 | Camm et al. | 446/14 |

FOREIGN PATENT DOCUMENTS

| | | | |
|---|---|---|---|
| 0032843 | 7/1981 | European Pat. Off. | 446/301 |
| 1120840 | 7/1956 | France | 446/296 |

Primary Examiner—Robert A. Hafer
Assistant Examiner—Danton D. DeMille

[57] ABSTRACT

In a toy, an image of expanding and contracting heart (309',311') is produced by a separate generator (207), or in response to sensing a pulse beat of a child by a sensor (3,403,405), or in response to sensing at least one parameter of environment by environment sensors (511-513).

17 Claims, 11 Drawing Sheets

TOY

The instant application is continuation-in-part application of my prior application 06/734,173 filed May 15, 1985, which issued July 22, 1986 as U.S. Pat. No. 4,601,668 and also relates to my copending application Ser. No. 06/831,711, filed Feb. 21, 1986 and Ser. No. 06/887,365, filed July 17, 1986.

TECHNICAL FIELD

The present invention relates to a toy. The term "toy" is used here to identify a toy to be played with, of any form and nature.

BACKGROUND ART

Many different toys are known in the art and used by children for amusing and educational purposes. One of the main purposes of giving a toy to a child is to generate attachment between the child and the toy. The closer the relationship between the child and the toy, the higher will be educational and humane value of the toy. This is especially, but not exclusively, true with respect to the toys formed as dolls. In dolls, it is very important if a doll imitates a real human being by producing certain visual or sound features resembling those of human beings or animals, by reacting to environmental factors or irritants similarly to human reactions. It is also important if a doll reacts to rocking similarly to a child which is rocked to sleep. Another advantage is the ability to play doctor by applying a toy stethoscope to a doll, which however in conventional toys is very limited.

DISCLOSURE OF THE INVENTION

Accordingly, it is an object of the present invention to provide a toy which has an increased attractiveness and educational value.

In keeping with these objects and with others which will become apparent hereinafter, one feature of the present invention resides in a toy which has a body part and electronic means, including means forming an image of expanding and contracting heart in the body part. The image of expanding and contracting heart in the toy is very attractive for children. Especially in human-like dolls and toy animals this image reminds the children about the fact that their doll or toy animal also has a heart and must be taken care of.

Another feature of the present invention is that the above image is produced in response to sensing at least one parameter of environment (temperature, smoke, noise, etc) by a sensor in the toy. Especially for dolls, this feature imitates humane or animal reaction to the environment and its irritants.

A further very important feature of the present invention is that a sensor senses pulse beats of a user, and signals (the image of expanding and contracting heart, pulse sounds) are produced in response to the sensed pulse beats of a user.

BRIEF DESCRIPTION OF THE DRAWINGS

The details of the invention will be described in connection with the accompanied drawings, in which.

BEST MODE FOR CARRYING OUT THE INVENTION

The present invention is illustrated by a toy which has a doll and a stethoscope. However, any toy can be designed in accordance with the features of the present invention, not necessarily with a stethoscope and even not necessarily formed as a doll.

Figure 1:
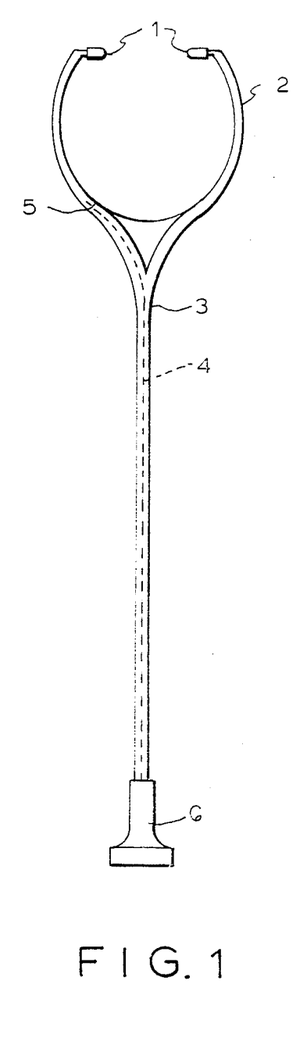
FIG. 1 is a view showing a stethoscope of a toy in accordance with the present invention.

FIG. 1 shows a stethoscope of a toy in accordance with the present invention, which has earphones 2, a plastic tube 3 and an electronic device 6. The earphones are used here both to function as conventional earphones and also as one pole electrode of a heart pulse transducer as will be explained hereinbelow. A signal lead 4 is connected with a metal tube of the earphones at point 5 and extends through the rubber tube 3 to the electronic device 6. The earphones are provided with metal tips 1 for better electrical contact with the child's ears. The tube 3 serves as a sonic conductor between the earphones and a sonic transducer 16 shown in FIG. 2 which is a part of the electronic device. It is also used for the signal lead 4.

Figure 2:
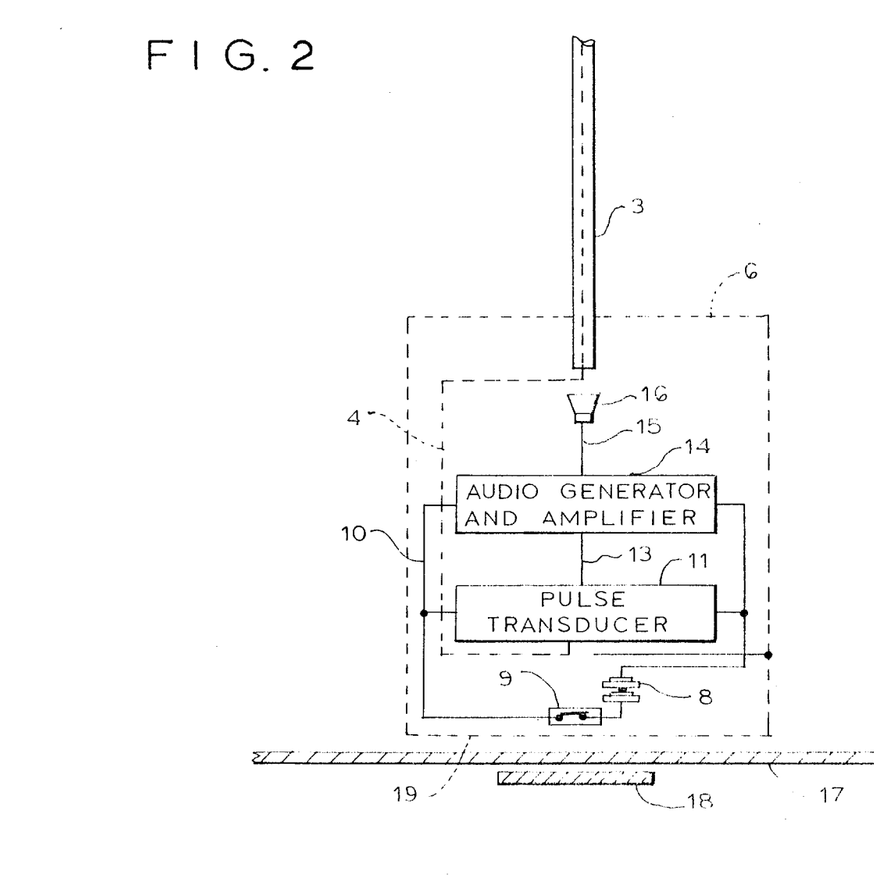
FIG. 2 is a view showing electronic means and a magnetic member for turning it on, associated with a doll and the stethoscope of the toy.

The electronic device 6 is arranged in a round metallic cover as shown in FIG. 2. The device includes a battery 8 of a watch type, connected through a reed switch 9 and by leads 10 and 11 to a heart pulse transducer 12 and an audio generator and amplifier 14. The sonic transducer 16 is connected to the audio generator and amplifier by a lead 15. A small magnetic member 18 is installed under the surface of a doll 17 in the region of an imaginary heart. When the electronic device 6 has its base 19 brought into this region of the doll, the magnetic member 18 turns on the reed switch 9 and the device begins to work.

Figure 3:
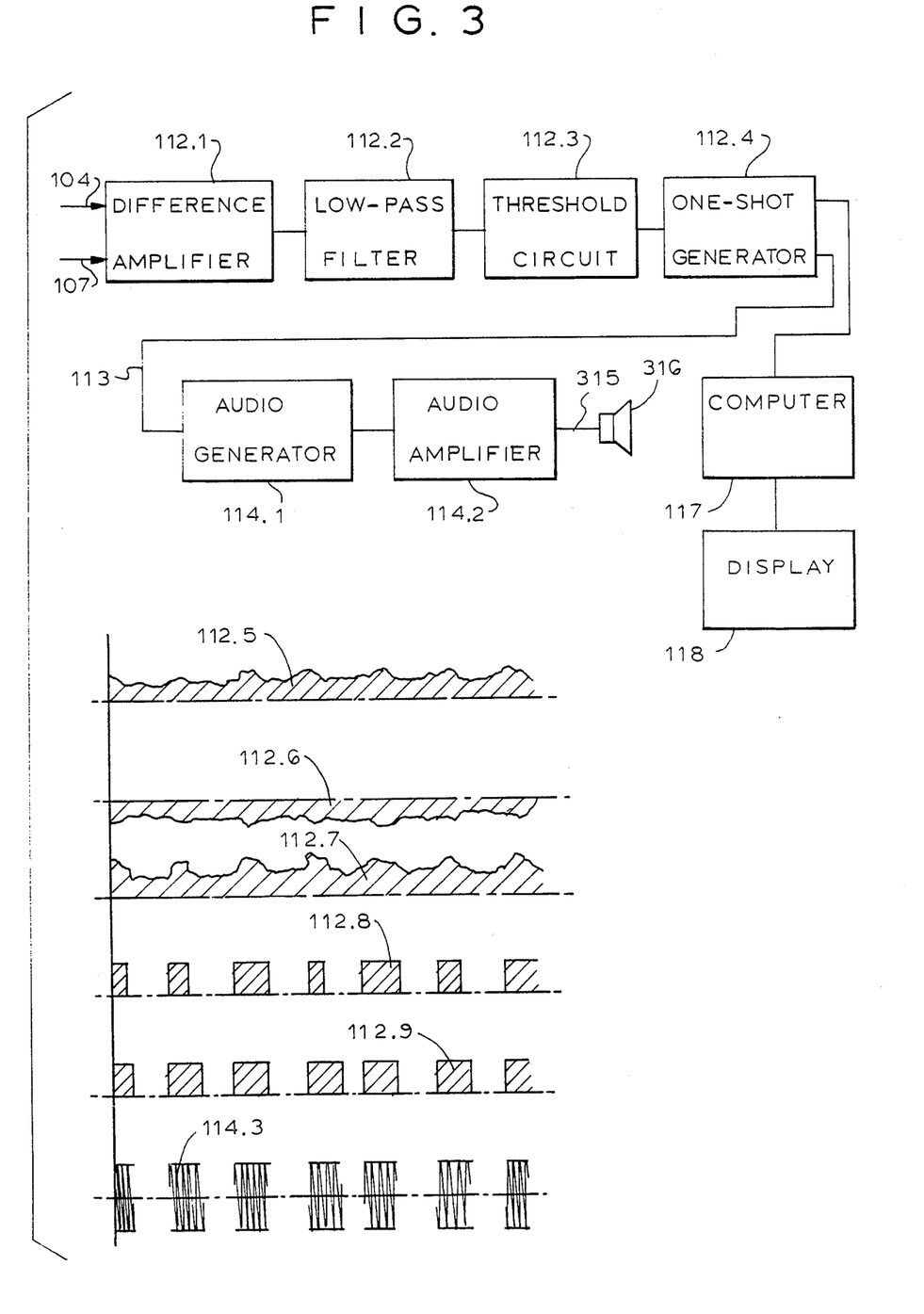
FIG. 3 is a view showing the details of an electronic device of the electronic means of FIG. 2.

FIG. 3 shows some details of the electronic device 6 and its waveforms. The transducer 12 includes a difference amplifier 112.1, a low-pass filter 112.2, a threshold circuit 112.3, a one-shot pulse generator 112.4, and waveforms 112.5–112.9. The audio generator and amplifier 14 includes an audio generator 114.1, an amplifier 114.2 and a waveform 114.3. The heart pulse transducer 12 is connected by a lead 113 with the audio generator and amplifier 14. The input lead 104 extends from the earphones as a first bioelectrical electrode, and the lead 107 is connected to the metal cover of the electronic device 6 as a second electrode. They transfer bioelectrical signals 112.5 and 112.6 to the difference amplifier 112.1. These signals are amplified and go through the low pass filter 112.2. Signal 112.7 is applied to the threshold circuit which generates square pulses 112.8. A square pulse train is fed to the one-shot pulse generator 112.4 to produce a constant amplitude and constant width pulse train 112.9. The pulse train 112.9 sets the audio generator 114.1 to produce an audio signal 114.3. The audio signal 114.3 is amplified by the audio amplifier 114.2 and feeds the sonic transducer 116 via the lead 115 to convert the electrical signals to sound. The sonic signals of approximately 200 cycles per second are applied through the rubber tube 3 to the earphones. A child actually hears his or her own heart beat, when he monitors the doll's pulse.

Figure 7:
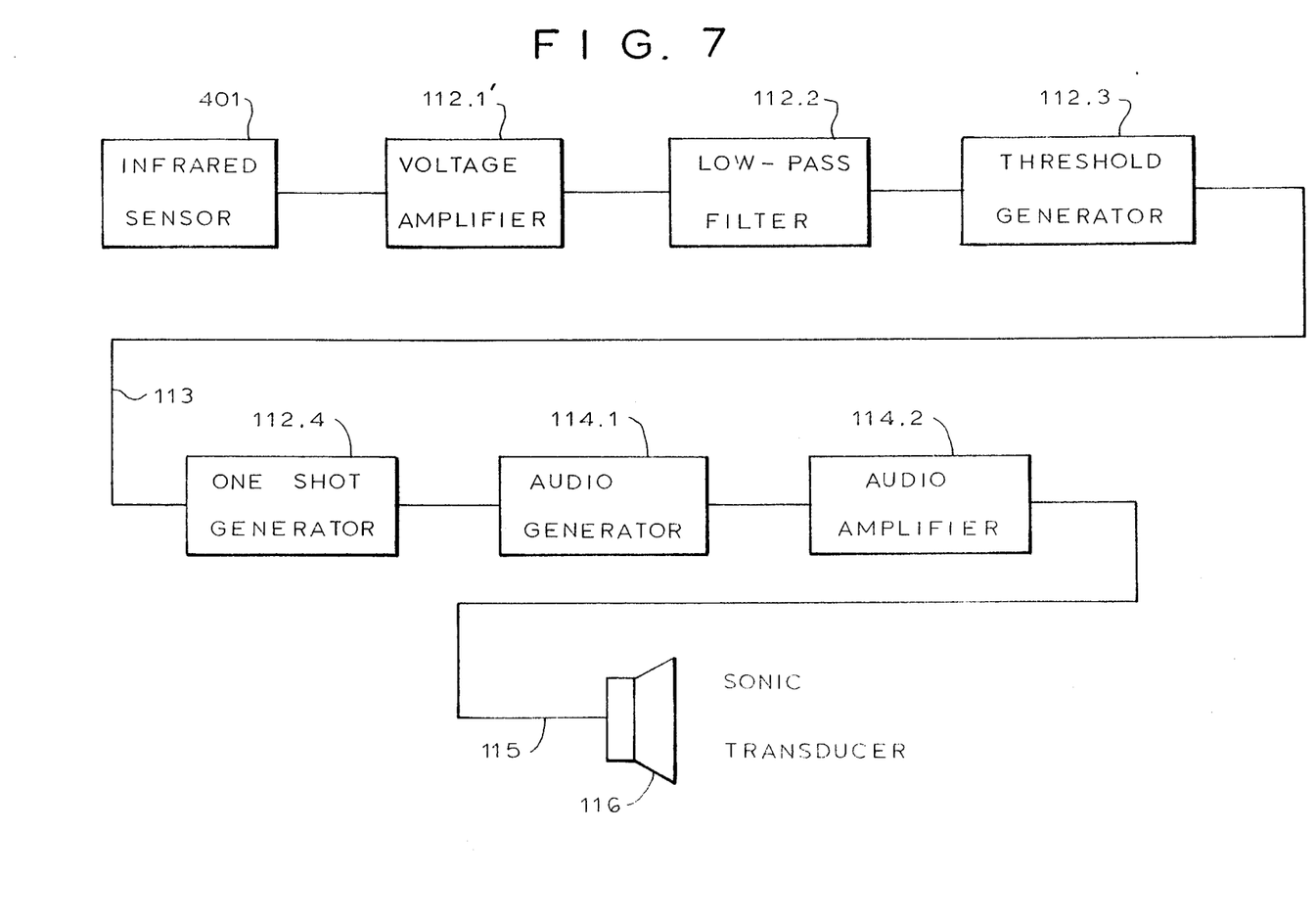
FIGS. 7 and 8 illustrate still further embodiments of the inventive toy.

Instead of the biopotential electrodes as described above, an infrared transmission transducer on an ear lobe or a finger of a child can be used, as shown in FIG. 7. In this case a difference amplifier 112.1 is replaced by a conventional voltage amplifier 112.1', and the waveform 112.5 will not be used.

Figure 4:
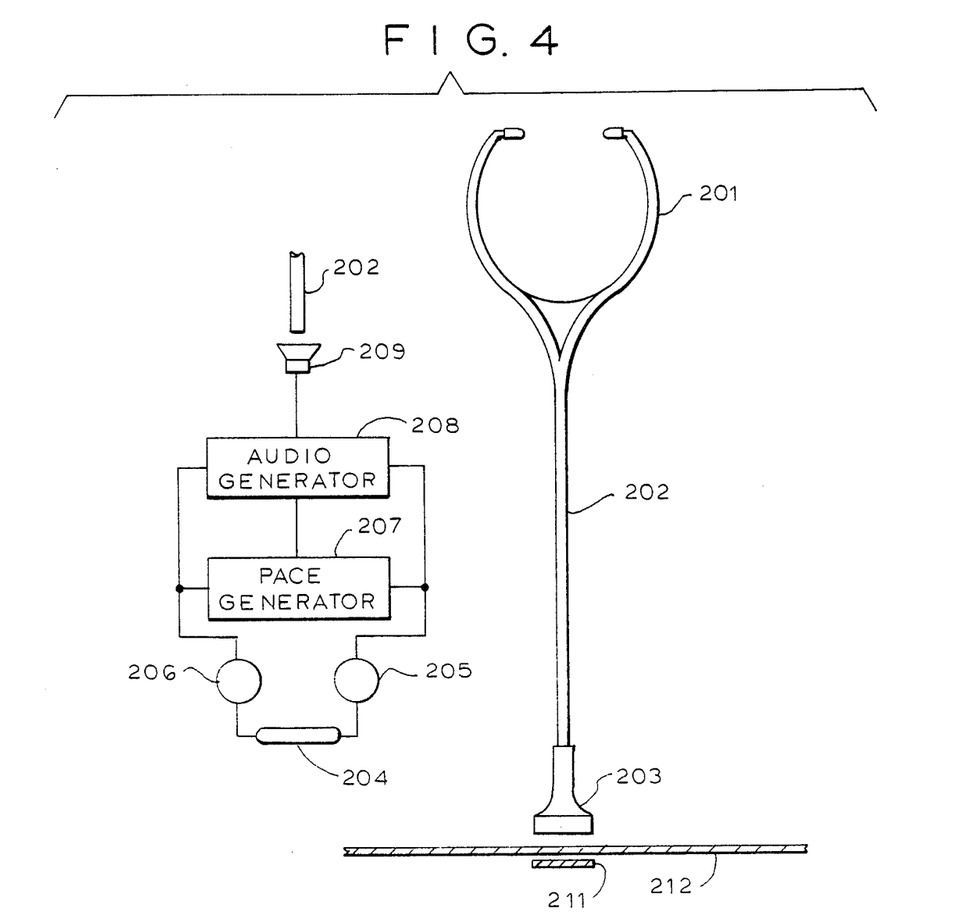
FIG. 4 is a view showing the toy in accordance with another embodiment of the invention.

The toy of a somewhat simpler type is shown in FIG. 4. Earphones of medical type 201 are used with a rubber tube 202 and an electronic device 203. A small magnetic member 211 is installed under the surface of a doll 212, as described above, and operates in the same manner. The magnetic member turns on the reed switch and the electronic device which includes batteries 205 and 206, a pace generator 207, an audio generator 208 and a sonic transducer 209. A human pulse is imitated here by the pace generator 207 which controls the audio generator 208. It produces the audio signal transduced by the sonic transducer 209. This sound passes through the tube 202 to the earphones. When the device is removed from the region of the magnetic member, its operation is interrupted.

Figure 5:
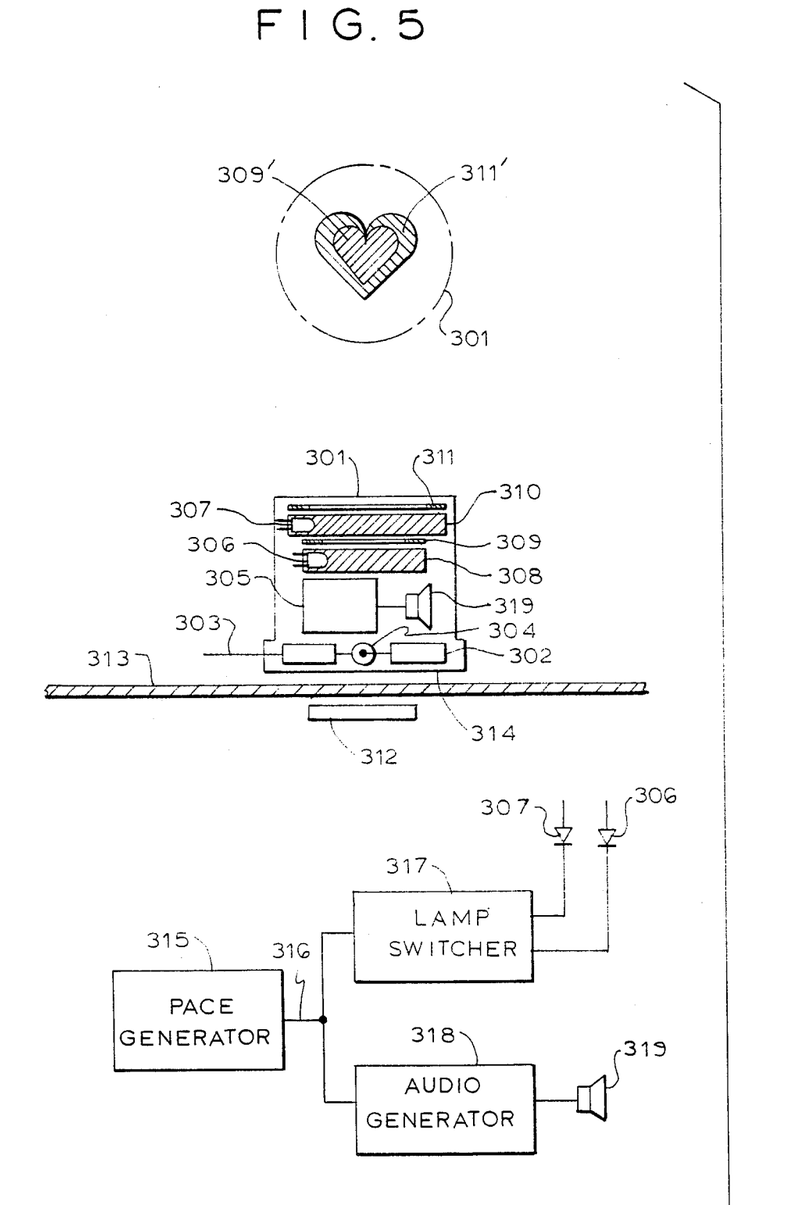
FIG. 5 is a view showing the toy in accordance with a further embodiment of the invention, for producing video signals.

FIG. 5 shows a toy in which heart activity of the doll's heart is illustrated visually in a new inventive manner. The toy has a plastic or metallic cover 301, batteries 302, 303 of a watch type, a reed switch 304, an electronic device 305, light emitting diodes 306,307, light conductors 308,310 and masks 309,311. As in the case of the above described stethoscope, a small magnetic member 312 is installed under the surface of the doll 313. When the device is applied by its base on the region of the doll heart where the magnetic member is arranged, the magnetic member 312 turns the reed switch 304 and the device begins to operate. A pace generator 315 which is a part of the electronic device 305 produces rhythmic pulses of a square form, at about 70 cycles per minute. These pulses control, via a lead 316 both a lamp switcher 317 and an audio generator 318. The lamp switcher turns on either of the light emitting diodes 306 or 307, and turns them off. The diodes are lit alternatingly. The diodes are set in color plastic glass components. When either diode 306 or diode 307 is on, it illuminates the whole area of the respective light conductor 308 or 310. The masks are installed in front of both light conductors 308 and 310 and formed as a smaller heart and a bigger heart respectively. When either diode 306 or 307 is on, the smaller heart 309' or the bigger heart 311' will be lit. On the other hand, the smaller heart can always be on, while the greater heart can be turned on and off. The pulses from the pace generator control the audio generator 318 as well. This generator produces an audio signal, about 800 cycles per second and is connected directly to a sonic tranducer 319. The operation of the audio generator 318 is synchronized with lighting of the hearts, for example of only the bigger heart, and is on when the latter is on.

It is to be understood that the operation of the toy shown in FIG. 5 can be performed in accordance with pulse beats of a child, by connecting it to a child pulse sensors as described with reference to FIGS. 1–3 and 7. In this case the audio generator 318 and the lighting of the hearts will be performed in accordance with the pulse beats of the child, or a person who plays with the child.

As shown in the right upper corner of FIG. 3 the toy can additionally include a computer 117 connected with the one-shot generator, and a display 118 connected with the computer. In this construction the pulse beat can be displayed, for example in a digital form, on the display. Therefore, the toy can simultaneously serve as a conventional human pulse monitoring device, thus performing not only the playing function, but also the function of a medical device.

The range of use of the toy considerably widens when the child is involved in serious relations with adults or with other children by playing the role of a physician. In addition the child can take a pulse of his or her pets.

Figure 6:
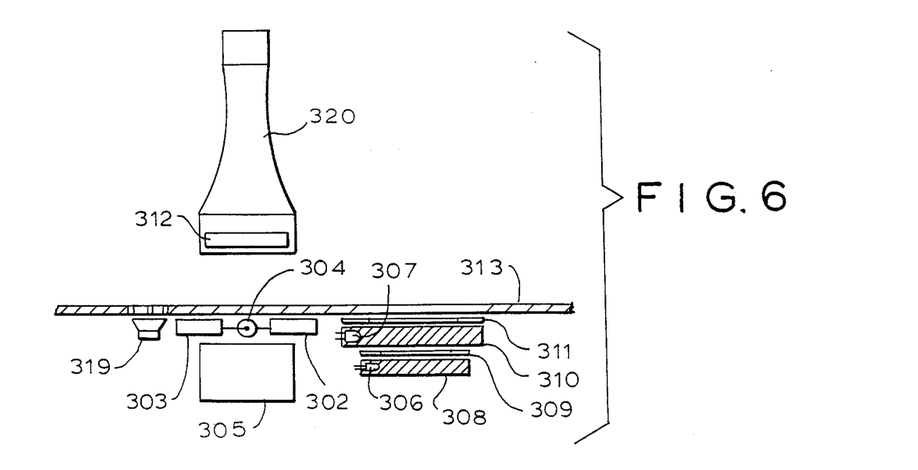
FIG. 6 shows the toy substantially corresponding to that of FIG. 5, but in correspondence with a different embodiment.

FIG. 6 shows a toy which corresponds to the toy of FIG. 5 with the only difference that the magnetic member is installed in a small handle 320, whereas the other parts of the electronic device are installed in the doll. The parts are identified with the same reference numerals, and the toy operates in the same manner as the toy shown in FIG. 5.

Figure 8:
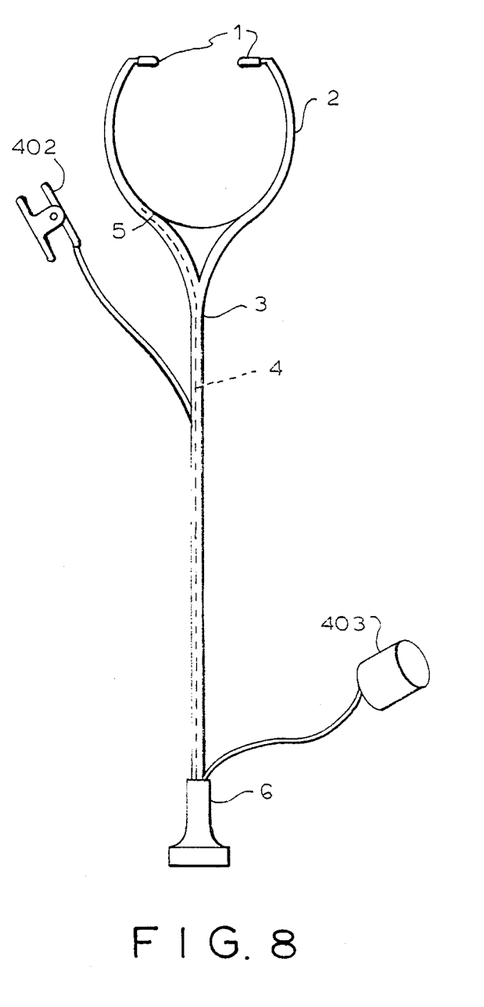

Finally, FIG. 7 shows the toy in which an infrared sensor 401 is used, attachable to an ear lobe or settable on a finger. FIG. 7 shows a block-diagram of this embodiment. FIG. 8 shows the stethoscope of the toy with the respective sensors which can be used alternatingly. A sensor 402 is attachable to an ear lobe, while a sensor 403 is settable on a finger. Instead of, or in addition to the embodiments described above, in which the magnetic member is located in the region of the doll heart and the video signals are represented by the contracting and expanding heart, there can be a magnetic member located in the region of the doll's wrist and the video signals can be represented by a flashing point-like light imitating blood in a vein.

The magnetic member can be arranged on the doll's body, inside the doll's body, and also on the clothes of the doll, in the region of the doll's heart. The magnetic member on the body and on the clothes can be heart-shaped.

Figure 9:
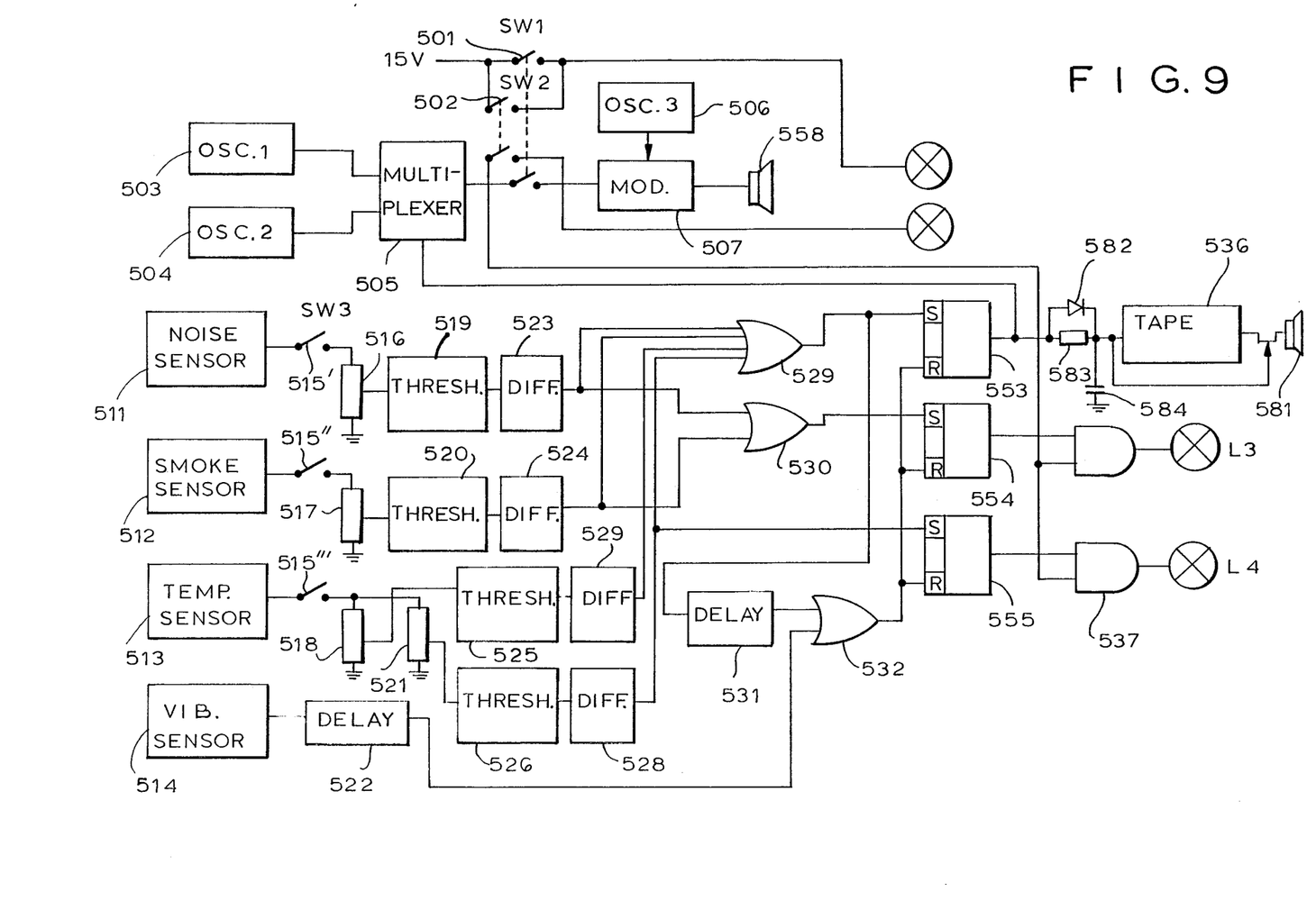
FIG. 9 is a block-diagram of a toy in accordance with an additional important embodiment.
Figure 10:
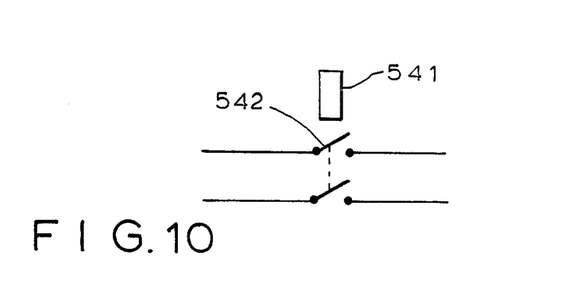
FIGS. 10 and 11 are views showing switches which cooperate with a toy stethiscope of the toy of FIG. 9, to actuate the toy, for example a doll, respectively temporarily or permanently.

The toy in accordance with a further embodiment shown in FIG. 9 supra operates in response to at least one parameter of environment in the vicinity of the toy, sensed by sensing means. The electronic means includes two switches 501,502, two generators (oscillators) 503,504 which generate impulse signals of different frequency, a multiplexer 505, a generator (oscillator) 506, a modulator 507, a sound transmitter 508, and two light sources 509,510 for example formed as light-emitting diodes corresponding to those of FIG. 5 and respectively associated with light conductors and masks to form a smaller heart and a greater heart and to produce an image of expanding and contracting heart during respective operation.

Figure 15:
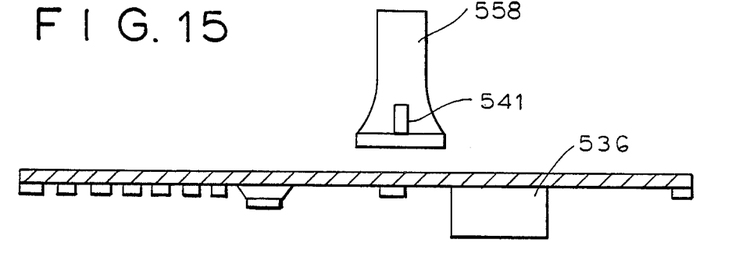
FIG. 15 shows arrangement of the respective parts of the toy of FIG. 9, for example inside a housing of a doll.

The toy can include a doll with a wall shown in FIG. 15 and a stethoscope 558 which is provided with a magnet 541. The above switches 501 and 502 are magnetically operated switches. When the stethoscope is applied to the doll so that the magnet 541 approaches the switch 501, the switch 501 is turned on. An impulse signal generated by the generator 506 (for example approximately 3000 Hz) is amplitude-modulated by another impulse signal generated by the generator 503 (approximately 1.2 Hz) which is supplied to the modulator 507 through the multiplexer 505. As a result of this, a pulsating sound is produced in the sound transducer 508, which imitates the frequency of pulse beat of heart. At the same time the light source 509 (light-emitting diode) is permanently turned on, while the other light source 510 (light-emitting diode) emits pulsating light with the frequency of the generator 503 (1.2 Hz) or in the other words the light, source 510 is periodically on and off, thus forming an image of expanding and contracting heart as described hereinabove.

The switch 501 is arranged for example at the left side of the doll's chest. When the stethoscope 558 is withdrawn from the switch 501, the sound (508) and the light (509, 510) pulsation of the doll's "heart" stops.

Figure 11:
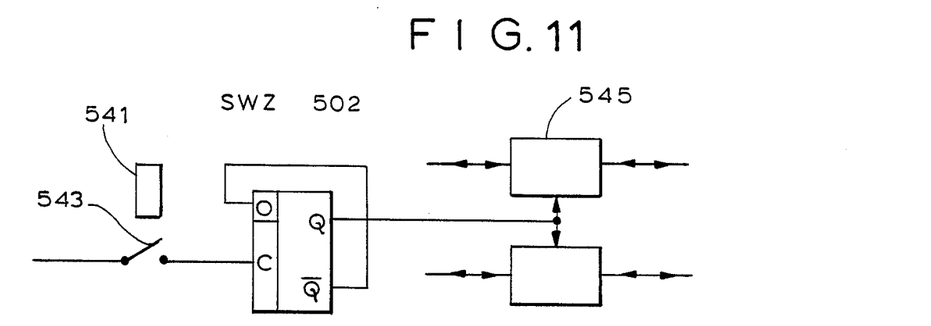

The switch 502 is arranged in another area, for example at the right side of the doll's chest. It is shown in detail in FIG. 11 and includes a switching member 543, a trigger 544, and a transistor switch 545. With each approach of the magnet 541 of the stethoscope 558 to the switch 502 it changes its position from closed to open and vice versa. By means of the switch 502, a child can turn on the sound (508) and light (509, 510) pulsation of the doll's heart for a permanent time, and they will not immediately turn off as in the case of the actuation by means of the switch 501.

The above described elements together form one part of the electronic means of the toy shown in FIG. 9. Another part of the electronic means includes four sensors 511, 512, 513, 514, wherein 511 is a noise sensor, 512 is a sensor of smoke, 513 is a sensor of temperature and 514 is a sensor of rocking. The sensors 511-514 sense respective parameters explained above, while the sensors 511-513 actually sense parameters of an environment in the vicinity to the toy, for example a doll. Each of the sensors 511-513 can be turned off by switches 515', 515'', 515''' respectively so that a respective sensor does not operate for sensing its parameter of the environment, when desired. The sensor 514 is preferably always operative for sensing. The turning off of the sensors 511-513 can be performed manually by acting directly on the respective switch 515'-515'''. On the other hand, it can also be performed by the magnet 541 of the stethoscope 558 since the switches are magnetically operated.

The sensors 511-513 are known sensors which are used in the arts for sensing respectively noise, smoke, temperature and producing impulse signals when the above parameters exceed a predetermined level or threshold. The sensitivity of each sensor 511-513 (their threshold) can be adjusted for example by potentiometers 516,517,518,521. The impulse signal pass further through threshold devices 519, 520, 525, 526 and differentiators 523, 524, 527, 528. Then a single impulse is separated (formed) when the impulse signal exceeds the threshold.

When the impulse signal is supplied from at least one of the sensors 511-513, a trigger 533 turns its position (switches) and actuates a delay element 531 which is set to provide a delay of approximately 30-40 sec. As a result of this, a sonic transducer 536 is actuated and it produces a sound which imitating for example crying performed during the time determined by the delay element. The multiplexer 505 passes the impulse signal with a frequency of approximately 2 Hz from the generator 504 (higher than 1.2 Hz from the generator 503) and the light sources 509 and 510 produce the image of expanding and contracting heart with a higher frequency. In other words, when the toy such as a doll for example, "experiences" excessive temperature, "is subjected" to high noise, or is "near" a smoking person its heart beat is faster and it cries.

When the impulse signal is supplied from the sensor 511 or 512, a trigger 534 is actuated and a light source 539 is turned on with the frequency of 2 Hz. The light source is located for example in the region of the doll's stomach and when it is on, it produces the image of a "butterfly in the stomach" for example by association with a respective mask, thus imitating nervousness or fear when there is noise or smoke in the vicinity of the doll. The manner of forming the butterfly image can be the same as in the case of the image of expanding and contracting heart shown in FIG. 5, or any other manner. For example liquid crystal displays can be used for the formation of the butterfly image. The same is true with respect to the image of expanding and contracting heart: it also can be formed on liquid crystals, etc.

When the impulse signal is supplied from the temperature sensor 513, which takes place when the temperature of the environment decreases (it becomes cold because the doll is outside of a house, undressed by a child, etc.), a trigger 535 is actuated and a light source 540 is turned on and operates with the frequency of 2 Hz. The light source 540 is located in the area of the doll's throat and when it is on, it produces the image of a "frog in the throat" of the doll, thus imitating that the doll is cold.

Stopping (turning off) of each video signal (the images of expanding and contracting heart, the butterfly, the frog) or audio signal (heart beat, crying) emitted by the toy can be performed in 30-40 second as described hereinabove, from the signal supplied by the delay element 531. On the other hand, this can be performed in response to the impulse signal supplied from the sensor 514 with a delay of 5-9 seconds, for example, produced by a delay element 522. The sensor 514 is a rocking sensor and it operates when a child rocks (or perform shaking movements) the doll. Generally, when a child does not rock the doll, it continues crying and exhibiting the heart, frog and butterfly images. When the child rocks the doll, these signals stop. Thus the child's care (rocking the doll) silences the doll or other toys.

Figure 12:
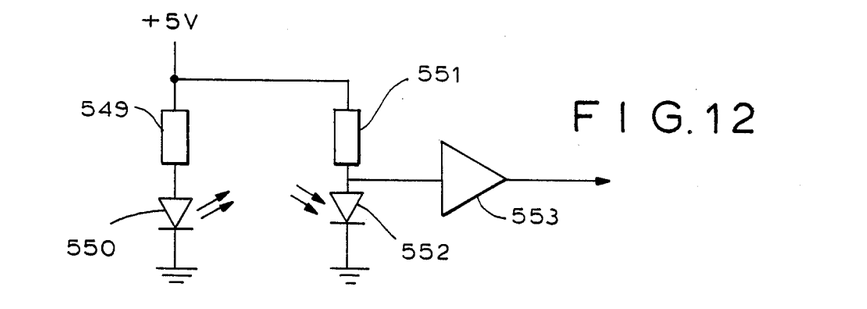
FIGS. 12 and 13 are views showing rocking sensors which senses rocking of the toy of FIG. 9, by a child.
Figure 13:
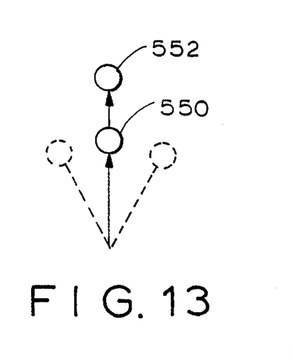

An electrical rocking sensor is shown in FIGS. 12 and 13. When the doll is not rocked, light from light-emitting diode 550 passes to a photo-diode 552 and there is no signal at the output of the sensor. When the doll is rocked, the light-emitting diode 550 swings for example on a flat spring, the light does not pass to the photodiode 552 and there is no signal at the output of the sensor. The light-emitting diode preferably swings in a vertical plane transversely to the doll's body when the doll lies on its back. This is how it must be oriented so that rocking of the lying doll from right to the left or vice versa actuates the sensor 514.

Figure 14:
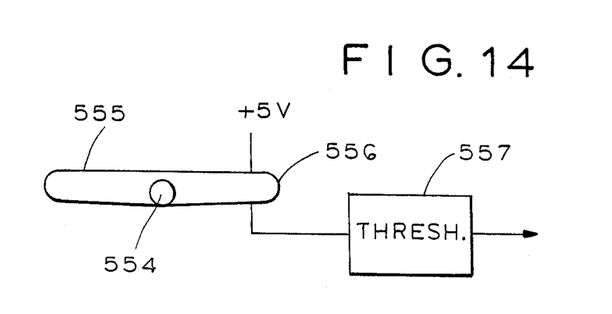
FIG. 14 is a view showing a rocking sensor of the toy, in accordance with another embodiment of the present invention.

The rocking sensor in accordance with another embodiment is shown in FIG. 14 which is a vertical cross section of the doll, transversely to its body, when the doll lies on its back. The doll has a channel 555 with a small depression in its bottom. When the doll is not rocked, a current-conductive ball rests in the depression of the channel 555 and electrical contacts 556 are open. When the doll is rocked by a child, the ball 554 moves to the right and closes the contacts 556 thus producing a signal at the outlet of the sensor.

A tape recorder 536 is provided with a sound transducer 581 and a unit which includes a diode 582, a resistor 583, a capacitor 584 and a transistor 585. When the impulse signal is supplied to the tape recorder 536 it passes momentarily to the tape recorder through the diode 582 and turns the tape recorder so that the doll "cries" or another toy produces a different desired sound. when the child rocks the doll and the signal from the rocking sensor resets the trigger 533, the doll does not stop "crying" momentarily, since the capacitor discharge cannot take place through the diode 582, but instead it takes place through the resistor 583. Moreover, the resistance on the transistor increases, and the crying not only stops after a certain delay, but also gradually weakens so that the sound of crying becomes gradually less and less loud.

It should be emphasized that the images of the "butterfly in the stomach" and "frog in the throat" correspond to the accepted idiomatic expression in the English language, and therefore teach the children their heritage; and have a great educational value.

Figure 16:
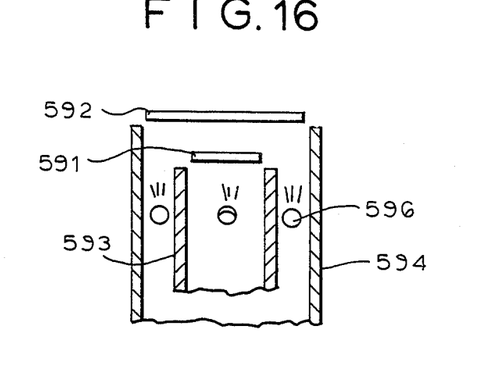
FIG. 16 is a view schematically showing a heart imitating display in accordance with another embodiment of the present invention.

FIG. 16 shows another embodiment of the display which forms the image of expanding and contracting heart. It has a smaller heart-shaped member 591 and a bigger heart-shaped member 592 associated with an inner tube 593 and an outer tube 594. The heart-shaped members are transparent and colored, provided with light sources for example as light-emitting diodes 596 behind them. The light source inside the inner tube 593 can be always on, while the light source between the inner tube and the outer tube can be alternatingly on and off. Therefore, the image of expanding and contracting heart is produced.

The electrical means can be supplied with power for example from a battery, which can be rechargeable. It can also be supplied from a conventional electrical network.

Figure 17:
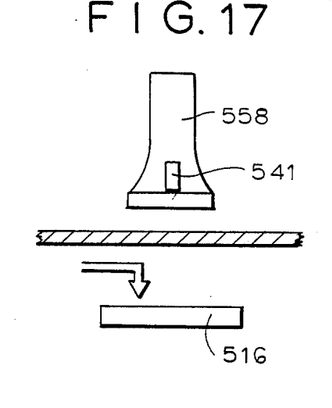
FIG. 17 shows adjustment of the sensitivity of sensors which sense environmental parameters and actuate the electronic means of the toy in accordance with the present invention.

FIG. 17 shows how the level of sensitivity of the sensors can be adjusted from outside the doll or another toy. A movable adjusting member of the potentiometer, for example of the potentiometer 516, can be displaced along the potentiometer by the magnet of the stethoscope movable outside the doll near the adjusting member, so as to act through the wall of the doll.

Figure 18:
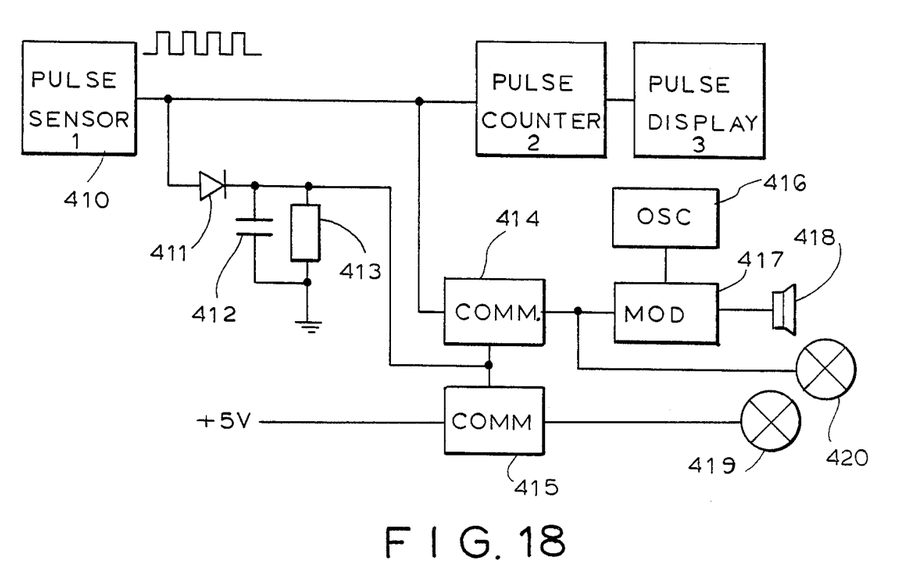
FIG. 18 schematically shows a toy in which the pulse beat of a child directly controls the video and audio signals produced by the toy.

Finally, FIG. 18 schematically shows a toy in which pulse beat of a child directly controls the video and audio signals produced in the toy. When a child activates a pulse sensors 410 which can be arranged, for example, on the outer surface of the doll, a signal is supplied through a diode 411 and an integrating circuit 412, 413 to commutators 414 and 415 and close them so that the signal passes through them. A generator 416 generates high frequency signal which is modulated in a modulator 417 and supplied to a dynamic 418 producing sounds which correspond to the heart beat. While a light source 419 is supplied with a constant frequency, a light source 420 is supplied with a modulated frequency from 414, 417, for example to produce an image of expanding and contracting heart as in FIG. 5.

The invention is not limited to the details shown since various modifications and structural changes are possible without departing in any way from the spirit of the present invention.

What is desired to be protected by Letters Patent is set forth in particular in the appended claims.

I claim:

1. A toy, comprising a body part; and means for forming a picture inside the body part and displaying the picture to the outside of the body part, wherein the picture is an image of an expanding and contracting heart and wherein said picture forming means include two heart-shaped elements formed so that one of said heart-shaped elements has a smaller size than the other of said heart-shaped elements; and further comprising means for alternatively lighting said heart-shaped elements so as to form a picture of said heart.

2. A toy as defined in claim 1, wherein said means for forming a picture also includes means producing audio signals which substantially imitate pulse beats of a heart.

3. A toy as defined in claim 1, wherein said body part includes a doll element and a activating means operative for activating said means for forming a picture by turning on said means for forming a picture when said activating and said body part are brought into proximity with one another.

4. A toy as defined in claim 3, wherein said means for forming a picture is arranged in the region of an imaginary heart of said doll element, and said activating means being operative to turn on said means for forming a picture when brought into proximity to said region of said doll element.

5. A toy as defined in claim 3, and further comprising switching means arranged to also activate said means for forming by turning on said means for producing a picture, wherein a frequency of said picture produced by said picture producing means in response to turning on by said activating member is higher than a frequency of said picture in response to turning on by said switching means.

6. A toy as defined in claim 1, wherein said means producing a picture includes means producing a sound of crying.

7. A toy as defined in claim 6, wherein said body part includes a doll element with a rocking sensor formed so that when said doll element is rocked said sensor stops production of said sound of crying.

8. A toy as defined in claim 7; and further comprising delay means connected with said means for producing a sound of crying and formed so that when rocking of said doll element stops the production of said sound of crying still continues for a predtermined time.

9. A toy as defined in claim 7, and further comprising means for gradually weakening said sound of crying until it completely disappears, after the rocking of said doll element has been stopped.

10. A toy as defined in claim 1, wherein said body part includes a doll element, said means producing a picture including means forming an image of a butterfly in a stomach area of said doll element.

11. A toy as defined in claim 1, wherein said body part includes a doll element, said means producing a picture including means forming an image of a frog in a throat area of said doll element.

12. A toy as defined in claim 1, wherein a signal generator means generates audio signals corresponding to a pulse beat of the image of the expanding and contracting heart.

13. A toy as defined in claim 1, wherein a signal generator means also generates video signals corresponding to pulse beats of the image of the expanding and contracting heart.

14. A toy as defined in claim 1, wherein the means for forming a picture forms a plurality of pictures in the toy.

15. A toy as defined in claim 14, wherein one of the plurality of pictures is a flashing light imitating blood in a vein of the toy.

16. A toy as defined in claim 14, wherein one of the plurality of pictures is an image of a frog in a throat area of the toy.

17. A toy as defined in claim 14, wherein one of the plurality of pictures is an image of a butterfly in a throat area of the toy.

* * * * *